United States Patent [19]

Okuda et al.

[11] 4,200,626
[45] Apr. 29, 1980

[54] HALOPLATINATE DENTAL COMPOSITION FOR PREVENTING AND INHIBITING DENTAL CARIES

[75] Inventors: Hirohisa Okuda, Nara; Nobutaka Hori, Uji, both of Japan

[73] Assignee: Toyo Seiyaku Kasei Co., Ltd., Japan

[21] Appl. No.: 942,809

[22] Filed: Sep. 15, 1978

[51] Int. Cl.² .................... A61K 7/16; A61K 33/24
[52] U.S. Cl. ........................... 424/51; 424/49; 424/131
[58] Field of Search .................. 424/49, 51, 131, 52

[56] References Cited

U.S. PATENT DOCUMENTS

1,077,854  11/1913  Paal et al. .................... 424/131

FOREIGN PATENT DOCUMENTS

2263751  11/1975  France ........................ 424/49

*Primary Examiner*—Douglas W. Robinson
*Attorney, Agent, or Firm*—Berman, Aisenberg & Platt

[57] ABSTRACT

A dental composition comprising, as an essential ingredient, water-soluble haloplatinate and a pharmaceutical carrier or diluent, prevents and inhibits dental caries. The composition exhibits its anticarious effect by inhibiting both digestion of the soft tissue in dentin with a protease and decalcification of the hard tissue in dentin with an acid.

11 Claims, No Drawings

HALOPLATINATE DENTAL COMPOSITION FOR PREVENTING AND INHIBITING DENTAL CARIES

The present invention relates to a dental composition for preventing and inhibiting dental caries. More particularly, the dental composition of the present invention exhibits its anticarious effect by inhibiting both digestion of the soft tissue in dentin (organic components) with a protease and decalcification of the hard tissue in dentin (inorganic components) with an acid.

To prevent dental caries, there has been used a water-soluble fluoride, for example sodium fluoride or another fluoride, such as stannous fluoride, sodium silicofluoride. The fluoride is formulated into a composition, for example, a solution suitable for a treatment, such as painting it on the tooth surfaces or mouth washing, and such treatment is often carried out in a primary school, a kindergarten, a dental clinic or the like. Further, there is also carried out a treatment, such as internal administration of a tablet containing the above fluoride or addition of the fluoride to tap water. These treatments obtain considerable results. However, the effect of the fluoride as a medicament is not always enough to prevent or inhibit dental caries.

The anticarious function or mechanism of the fluoride is established by many studies. That is, fluoride ion ($F^-$) derived from the fluoride is reacted with hydroxyapatite of the hard tissue in dentin to provide acid resistance to the tissue and, thereby, makes the tissue more resistant against dissolution by an acid produced by oral bacteria (decalcification). Thus, the anticarious effect of the fluoride is exhibited by inhibiting the degradation of the hard tissue. The foregoing treatments, therefore, expect the action of $F^-$ derived from the fluoride on the hard tissue in dentin.

However, dental caries cannot be fully illustrated merely by the degradation of the hard tissue. In addition to the hard tissue, there is present about 20% of protein as the soft tissue in dentin, most of which is collagen. Collagen is a stable protein and is not decomposed at the pH value of saliva in the mouth. Collagen is, however, decomposed by a certain protease, such as collagenase. Therefore, it is believed that dental caries occurs and advances as the result of not only the degradation of the hard tissue but also that of the soft tissue in dentin.

By this reason, as described above, the anticarious effect of the fluoride is insufficient since the effect merely depends upon the action of $F^-$ on the hard tissue and it is ineffective on the soft tissue in dentin.

Under these circumstances, we have intensively studied various medicaments having a significant effect for preventing and inhibiting dental caries and have found that certain platinum compounds impart soft-tissue resistance to protease digestion as well as increased hard-tissue resistance to acid dissolution.

One object of the present invention is to provide a dental composition for preventing dental caries. Another object of the present invention is to provide a dental composition for inhibiting advancement of dental caries. These and other objects of the present invention will become apparent from the following description.

To accomplish these objects, according to the present invention, there is provided a dental composition for preventing and inhibiting dental caries which comprises as an essential ingredient a water-soluble haloplatinate and a pharmaceutical carrier or diluent. The dental composition of the present invention is applied to tooth surfaces and exhibits a superior anticarious effect by inhibiting both protease digestion of soft tissue in dentin and acid decalcification of hard tissue in dentin.

The water-soluble haloplatinate to be used includes tetrahaloplatinate and hexahaloplatinate. The term "halo" used herein includes fluorine, chlorine, bromine and iodine. The cation which forms the salt includes an alkali metal, such as lithium, sodium or potassium; an alkaline-earth metal, such as calcium; and ammonium cation. Examples of these compounds are ammonium tetrachloroplatinate, ammonium hexachloroplatinate, potassium tetrachloroplatinate, potassium hexachloroplatinate, sodium tetrachloroplatinate, sodium hexachloroplatinate, ammonium hexabromoplatinate, potassium tetrabromoplatinate, potassium hexabromoplatinate, sodium hexabromoplatinate, potassium hexaiodoplatinate, sodium hexaiodoplatinate. In view of stability and application properties of the composition, tetrachloroplatinate and hexachloroplatinate, particularly, potassium tetrachloroplatinate and sodium hexachloroplatinate are preferable. The haloplatinate is formulated into the composition in an amount of not less than 0.01% by weight (as platinum), preferably about 0.1 to about 5% by weight, on the basis of the total weight of the composition.

The pharmaceutical carrier or diluent to be used includes water, glycerin, propylene glycol, polyethylene glycol (macrogol), ethyl lactate or a mixture thereof or the like.

The dental composition of the present invention can be prepared in a form, such as a solution, a liquid suspension, or an aqueous paste (such as macrogol ointment), suitable for local treatment of the tooth surface. The dental composition can be prepared by conventional techniques involving procedures, such as mixing and dissolving the ingredients, as appropriate to the desired form of the composition. Optionally, the dental composition can contain another ingredient, such as a stabilizer, a preservative or the like. We have also found that a certain alkali-metal halide (e.g. sodium chloride) is useful as stabilizer of the dental composition of the present invention. Moreover, it is preferable to adjust the pH of the composition within the range from neutral to weak acidic so as to improve the anticarious effect further.

To estimate the effect of the dental composition of the present invention, the following tests were carried out.

The ability to inhibit digestion of the soft tissue in dentin was estimated according to the method described by Yanagida et al [Yanagida et al, Shonishikagaku Zasshi, Vol. 9, page 39 (1971)]. That is, firstly, a certain amount of human decalcified dentin powder was treated with a composition to be tested for certain minutes and then unbonded excess components were removed by dialysis to obtain a sample powder. Then, opaque agar plates were prepared by adding the sample powder, and a protease (collagenase or trypsin) was added to the plates. The inhibiting ability was estimated by observing whether a clear zone was formed on the plate or not. The clear zone is formed by dissolution of the powder with the enzyme, and the formation thereof means digestion of the soft tissue in dentin.

The results are shown in Table 1. Each composition used in the test is an aqueous solution at pH 5.4.

Table 1

| Dental composition | | |
|---|---|---|
| Platinum compound | Platinum content (%) | Clear zone |
| $Na_2PtCl_6$ | 0.1 | None |
| | 0.01 | None |
| | 0.001 | Present |
| $K_2PtCl_4$ | 0.1 | None |
| | 0.01 | None |
| | 0.001 | Present |
| $K_2PtI_6$ | 0.1 | None |
| | 0.01 | None |
| | 0.001 | Present |
| $(NH_4)_2PtCl_6$ | 0.1 | None |
| | 0.01 | None |
| | 0.001 | Present |

As is clear from Table 1, the dental composition inhibits digestion of the soft tissue by a protease at the platinum content of not less than 0.01%. When a similar test was carried out using sodium fluoride, no inhibition of the digestion was observed.

The ability to inhibit decalcification of the hard tissue was also estimated according to the method described by Nishino [Nishino, Osaka University Shigaku Zasshi, Vol. 1, page 1 (1969)]. That is, firstly, a certain amount of human dentin powder was treated with a composition to be tested for certain minutes and then unbonded excess components were removed by washing with water to obtain a sample powder. Then, the sample powder was treated with an acid solution (decalcification) and the amount of calcium in the solution, which was dissolved in the solution by action of the acid, was determined (sample calcium content). Similarly, untreated dentin powder was added to an acid solution and the amount of calcium in the acid solution was determined (control calcium content). From these values, the inhibition rate of decalcification was calculated as follows:

Inhibition rate of decalcification (%) =
$$(1 - \frac{\text{Sample calcium content}}{\text{Control calcium content}}) \times 100$$

The results are shown in Table 2. Each composition used in the test is an aqueous solution containing 2% of platinum, but when the solubility of the platinum compound is lower than 2% (as platinum), an aqueous solution saturated with the compound is used as the composition (all of these are at pH 5.4). As a reference, a similar test was done by using an aqueous solution containing 2% of sodium fluoride (pH 5.4). The results are also shown in Table 2.

Table 2

| Decalcification time (hour) | Inhibition rate of decalcification (%) | | |
|---|---|---|---|
| | $Na_2PtCl_6$ | $K_2PtCl_4$ | NaF |
| 0.5 | 43.42 | 27.28 | 40.03 |
| 1.0 | 45.23 | 28.11 | 43.29 |
| 1.5 | 45.15 | 30.86 | 44.12 |
| 2.0 | 45.36 | 29.65 | 44.02 |
| 3.0 | 47.57 | 30.22 | 44.33 |
| 5.0 | 47.77 | 31.54 | 44.79 |
| 24.0 | 48.00 | 31.69 | 44.93 |
| 48.0 | 48.20 | 32.27 | 45.45 |

As is clear from Table 2, the dental composition of the present invention also inhibits decalcification of the hard tissue in dentin. Particularly, the composition containing $Na_2PtCl_6$ shows a superior inhibiting effect to that containing NaF at every decalcification time and the effect thereof is not decreased even though after 48 hours.

Further, the dental composition of the present invention is useful from a viewpont of toxicity since these platinum compounds have lower toxicity than that of NaF. For example, testing $LD_{50}$ in mice, NaF shows $LD_{50}$ (p.o.) of about 90 mg per kg of body weight. On the contrary, $Na_2PtCl_6$ shows $LD_{50}$ (p.o.) of 130 mg per kg of body weight and $K_2PtCl_4$ shows that of 97 mg per kg of body weight.

Moreover, it has found that the dental composition of the present invention has a bacterial activity and is very useful to prevent and inhibit dental caries. For example, in a bacteriological test using *Staphylococcus aureus* 209 P, the dental composition inhibited the bacterial growth at the platinum concentration thereof more than 150 to 300 ppm.

The dental composition of the present invention can be used by painting an appropriate amount thereof on the tooth surface and maintaining it as it is for certain minutes. This treatment is repeated at regular intervals of time. For example, in case of using the dental composition (solution) of the present invention for preventing dental caries, firstly, the tooth surface is thoroughly cleaned. Moisture is removed from the tooth to be treated and surrounding area, and a tube may be inserted into the mouth to drain saliva when too much saliva is secreted. Then, the tooth surface is wiped with a swab, dried with an air blow gun and then rubbed with another swab soaked by the dental composition. The composition is applied to the tooth surface for 3 to 4 minutes at a time. In case of using the dental composition for inhibiting advancement of dental caries, firstly, softened dentin of the decayed part of the tooth is removed (using a spoon excavator), and the tooth surface is cleaned and dried. Then, the composition is applied to the tooth surface for 3 to 4 minutes as described above. These treatments are repeated several times every two to seven days.

As described hereinbefore, the dental composition of the present invention exhibits its anticarious effect not only by inhibiting decalcification of the hard tissue in dentin but also inhibiting digestion of the soft tissue in dentin.

The following examples illustrate the present invention but are not to be construed as limiting the scope thereof.

EXAMPLE 1

| Ingredients | % by weight |
|---|---|
| Sodium hexachloroplatinate hexahydrate | 5.8 |
| Sodium chloride | 1.0 |
| Water | Adjust to 100% |

These ingredients were mixed and dissolved to give a solution, and the pH thereof was adjusted to 5.5 to obtain the desired liquid dental composition.

EXAMPLE 2

| Ingredients | % by weight |
|---|---|
| Sodium hexachloroplatinate hexahydrate | 2.9 |
| Sodium nitrite | 0.033 |
| Water | Adjust to 100% |

These ingredients were mixed and dissolved to give a solution, and the pH thereof was adjusted to 3.5 to obtain the desired dental composition.

EXAMPLE 3

| Ingredients | % by weight |
| --- | --- |
| Sodium hexachloroplatinate hexahydrate | 2.9 |
| Sodium chloride | 0.5 |
| Sodium nitrite | 0.033 |
| Water | Adjust to 100% |

These ingredients were mixed and dissolved to give a solution, and the pH thereof was adjusted to 4.0 to obtain the desired dental composition.

EXAMPLE 4

| Ingredients | % by weight |
| --- | --- |
| Sodium hexachloroplatinate hexahydrate | 5.8 |
| Propylene glycol | Adjust to 100% |

These ingredients were mixed and dissolved to give a solution, and the pH thereof was adjusted to 3.8 to obtain the desired liquid composition.

EXAMPLE 5

| Ingredients | % by weight |
| --- | --- |
| Sodium hexachloroplatinate hexahydrate | 5.8 |
| Sodium chloride | 5.0 |
| 50% Glycerin | Adjust to 100% |

These ingredients were mixed and dissolved to give a solution, and the pH thereof was adjusted to 5.0 to obtain the desired composition.

EXAMPLE 6

| Ingredients | % by weight |
| --- | --- |
| Sodium hexachloroplatinate hexahydrate | 5.8 |
| Sodium chloride | 5.0 |
| 50% Carbowax | Adjust to 100% |

These ingredients were mixed and dissolved to give the desired liquid composition.

EXAMPLE 7

| Ingredients | % by weight |
| --- | --- |
| Potassium tetrachloroplatinate | 4.26 |
| 0.05 M aqueous sodium dihydrogen phosphate solution | Adjust to 100% |

These ingredients were mixed and dissolved to give a solution, and the pH thereof was adjusted to 4.6 to obtain the desired liquid composition.

EXAMPLE 8

| Ingredients | % by weight |
| --- | --- |
| Potassium tetrachloroplatinate | 4.26 |
| Potassium chloride | 1.0 |
| Water | Adjust to 100% |

These ingredients were mixed and dissolved to give a solution, and the pH thereof was adjusted to 6.0 to obtain the desired liquid composition.

EXAMPLE 9

| Ingredients | % by weight |
| --- | --- |
| Sodium hexachloroplatinate | 2.0 |
| Macrogol 400 | 49.0 |
| Macrogol 4000 | 49.0 |

Macrogol 4000 was added to macrogol 400 and dissolved by warming at 60° C. To the mixture was added sodium hexachloroplatinate to give a solution. The solution thus obtained was solidified by cooling with stirring to give the desired paste composition.

What is claimed is:

1. A dental composition for preventing and inhibiting dental caries which comprises not less than 0.01% by weight (as platinum) of a water-soluble hexahaloplatinate or tetrahaloplatinate and an acceptable dental carrier or diluent.

2. A dental composition according to claim 1, wherein said composition contains about 0.1 to about 5% by weight (as platinum) of the haloplatinate.

3. A dental composition according to claim 2, wherein the haloplatinate is a compound selected from the group consisting of ammonium tetrachloroplatinate, ammonium hexachloroplatinate, potassium tetrachloroplatinate, potassium hexachloroplatinate, sodium tetrachloroplatinate, sodium hexachloroplatinate, ammonium hexabromoplatinate, potassium tetrabromoplatinate, potassium hexabromoplatinate, sodium hexabromoplatinate, potassium hexaiodoplatinate and sodium hexaiodoplatinate.

4. A dental composition according to claim 3, wherein the haloplatinate is potassium tetrachloroplatinate.

5. A dental composition according to claim 3, wherein the haloplatinate is sodium hexachloroplatinate.

6. A dental composition according to claim 1 having a neutral or weakly acidic pH.

7. A dental composition of claim 1 in the form of a liquid having an effective haloplatinate concentration.

8. A dental composition according to claim 1, which contains an alkali halide stabilizer.

9. A dental composition according to claim 8, wherein the alkali halide is sodium chloride or potassium chloride.

10. A method for preventing or inhibiting dental caries which comprises applying to a tooth surface a dental composition containing an effective concentration of a water-soluble hexahaloplatinate or tetrahaloplatinate.

11. A method according to claim 10 wherein the dental composition contains from about 0.1 to about 5 percent by weight (as platinum) of a haloplatinate selected from the group consisting of ammonium tetrachloroplatinate, ammonium hexachloroplatinate, potassium tetrachloroplatinate, potassium hexachloroplatinate, sodium tetrachloroplatinate, sodium hexachloroplatinate, ammonium hexabromoplatinate, potassium tetrabromoplatinate, potassium hexabromoplatinate, sodium hexabromoplatinate, potassium hexaiodoplatinate, and sodium hexaiodoplatinate.

* * * * *